(12) United States Patent
Nasarabadi

(10) Patent No.: US 7,867,713 B2
(45) Date of Patent: Jan. 11, 2011

(54) POLYMERASE CHAIN REACTION SYSTEM USING MAGNETIC BEADS FOR ANALYZING A SAMPLE THAT INCLUDES NUCLEIC ACID

(75) Inventor: Shanavaz Nasarabadi, Livermore, CA (US)

(73) Assignee: Lawrence Livermore National Security, LLC, Livermore, CA (US)

(*) Notice: Subject to any disclaimer, the term of this patent is extended or adjusted under 35 U.S.C. 154(b) by 443 days.

(21) Appl. No.: 12/106,390

(22) Filed: Apr. 21, 2008

(65) Prior Publication Data

US 2009/0263794 A1 Oct. 22, 2009

(51) Int. Cl.
C12Q 1/68 (2006.01)
C12P 19/34 (2006.01)
C12M 1/00 (2006.01)

(52) U.S. Cl. .................... 435/6; 435/91.2; 435/287.2

(58) Field of Classification Search .................. 435/6, 435/91.2, 287.2
See application file for complete search history.

(56) References Cited

U.S. PATENT DOCUMENTS

| | | | |
|---|---|---|---|
| 6,159,378 A | 12/2000 | Holman et al. | |
| 6,372,486 B1 | 4/2002 | Fripp | |
| 6,534,262 B1 | 3/2003 | McKernan et al. | |
| 6,617,105 B1 | 9/2003 | Rudi et al. | |
| 2002/0072061 A1 | 6/2002 | Chenchik et al. | |
| 2002/0072112 A1 | 6/2002 | Atwood et al. | |
| 2004/0018611 A1* | 1/2004 | Ward et al. | 435/287.2 |
| 2006/0057599 A1 | 3/2006 | Dzenitis et al. | |
| 2006/0094051 A1 | 5/2006 | Lee et al. | |
| 2006/0166190 A1 | 7/2006 | Xie et al. | |
| 2006/0222569 A1* | 10/2006 | Barten et al. | 422/100 |
| 2006/0281101 A1 | 12/2006 | Dzenitis et al. | |
| 2007/0092901 A1 | 4/2007 | Ligler et al. | |
| 2007/0184463 A1* | 8/2007 | Molho et al. | 435/6 |

(Continued)

FOREIGN PATENT DOCUMENTS

WO 2006/121997 * 11/2006

(Continued)

OTHER PUBLICATIONS

Jungkind,"Automation of laboratory testing for infectious diseases using the polymerase chain reaction—our past, our present, our future", Journal of Clinical Virology 20 (2001) 1-6.

(Continued)

Primary Examiner—Kenneth R. Horlick
(74) Attorney, Agent, or Firm—Eddie E. Scott; James S. Tak

(57) ABSTRACT

A polymerase chain reaction system for analyzing a sample containing nucleic acid includes providing magnetic beads; providing a flow channel having a polymerase chain reaction chamber, a pre polymerase chain reaction magnet position adjacent the polymerase chain reaction chamber, and a post pre polymerase magnet position adjacent the polymerase chain reaction chamber. The nucleic acid is bound to the magnetic beads. The magnetic beads with the nucleic acid flow to the pre polymerase chain reaction magnet position in the flow channel. The magnetic beads and the nucleic acid are washed with ethanol. The nucleic acid in the polymerase chain reaction chamber is amplified. The magnetic beads and the nucleic acid are separated into a waste stream containing the magnetic beads and a post polymerase chain reaction mix containing the nucleic acid. The reaction mix containing the nucleic acid flows to an analysis unit in the channel for analysis.

11 Claims, 2 Drawing Sheets

U.S. PATENT DOCUMENTS

2007/0292889 A1* 12/2007 Bailey et al. .................. 435/7.1
2008/0023388 A1* 1/2008 Cho et al. .................... 210/222
2008/0058991 A1* 3/2008 Lee et al. .................... 700/266

OTHER PUBLICATIONS

Kojima et al, PCR amplification form single DNA molecules on magnetic beads in emulsion:application for high-throughput screening of transcription factor targets, Nucleic Acids Research, 2005, vol. 33, No. 17 el50.

Morales et al, Fabrication and Characterization of Polymer Microfluidic Devices for Bio Agent Detection, Proc. of SPIE vol. 5716, (2005).

Wilson et al, A multiplexed PCR-coupled liquid bead array for the simultaneous detection of four biothreat agents, Molecular and Cellular Probes 19 (2005) 137-144.

Akutsu et al, Development of an Integrated Automation System with a Magnetic Bead-Mediated Nucleic Acid Purification Device for Genetic Analysis and Gene Manipulation. Biotechnology and Bioengineering, vol. 86, No. 6, Jun. 20, 2004.

Paladichuk A: "Isolating RNA: Pure and Simple", Scientist, Philadelphia, PA, vol. 13, No. 16, Aug. 16, 1999, pp. 1-9, XP002405256, ISSN: 0890-3670, the whole document, p. 1, last paragraph, figure 3.

* cited by examiner

POLYMERASE CHAIN REACTION SYSTEM USING MAGNETIC BEADS FOR ANALYZING A SAMPLE THAT INCLUDES NUCLEIC ACID

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to nucleic acid reactions and more particularly to polymerase chain reactions with high throughput flow through sample preparation using magnetic beads.

2. State of Technology

U.S. Pat. No. 6,372,486 for a thermo cycler to David M. Fripp issued Apr. 16, 2002 provides the following background information, "Traditionally, scientists have used the technique of the Polymerase Chain Reaction (PCR) to synthesize defined sequences of DNA. This generally involves a three step procedure: separation of the DNA to be amplified (template DNA); annealing of short complimentary DNA sequences (primers) to the template DNA and finally the addition of deoxynucleotides to the primer strands in order to copy the template DNA. This is usually performed in a thermal cycling machine where a cycle of three different temperatures is repeated approximately 25-35 times. Template DNA separation and synthesis steps occur at defined temperatures. However, the temperature at which the primer binds to the DNA, may need optimizing in order for this step to occur efficiently and achieve desirable PCR results. Primer annealing optimization experiments usually involve setting up a number of different experiments where only the primer annealing temperature is varied. The experiment may need to be performed 3 or 4 times in order to determine the optimum binding temperature. These experiments would have to be repeated each time a new set of primers was required for different PCRs. The development of a temperature gradient block enables the scientists to determine the optimum binding temperatures of several primer sets in a single experiment."

U.S. Patent Application Publication No. 2002/0072112 for a thermal cycler for automatic performance of the polymerase chain reaction with close temperature control to John Atwood published Jun. 13, 2002 provides the following background information, "Applications of PCR technology are now moving from basic research to applications in which large numbers of similar amplifications are routinely run. These areas include diagnostic research, biopharmaceutical development, genetic analysis, and environmental testing. Users in these areas would benefit from a high performance PCR system that would provide the user with high throughput, rapid turn-around time, and reproducible results. Users in these areas must be assured of reproducibility from sample-to-sample, run-to-run, lab-to-lab, and instrument-to-instrument."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a polymerase chain reaction method for analyzing a sample that includes nucleic acid. The method includes the steps of providing magnetic beads; providing ethanol; providing a polymerase chain reaction master mix; providing a flow channel, the flow channel including a polymerase chain reaction chamber, a pre polymerase chain reaction magnet position adjacent the polymerase chain reaction chamber, and a post polymerase chain reaction magnet position adjacent the polymerase chain reaction chamber; mixing a chaotropic agent with the magnetic beads so that the nucleic acid is bound to the magnetic beads; flowing the magnetic beads with the nucleic acid bound to the magnetic beads to the pre polymerase chain reaction magnet position in the flow channel; washing the magnetic beads with the nucleic acid bound to the magnetic beads at the pre polymerase chain reaction magnet position by flowing the ethanol in the flow channel so that it flows over the magnetic beads with the nucleic acid bound to the magnetic beads; flowing the magnetic beads with the nucleic acid bound to the magnetic beads in the flow channel into the polymerase chain reaction chamber; amplifying the nucleic acid in the polymerase chain reaction chamber; flowing the magnetic beads with the nucleic acid bound to the magnetic beads to the post polymerase chain reaction magnet position in the flow channel; sequestering the magnetic beads at the post polymerase chain reaction magnet position separating the magnetic beads and the nucleic acid into an analysis stream containing the magnetic beads and a post polymerase chain reaction mix containing the nucleic acid, flowing the magnetic beads to waste in the flow channel; and flowing the post polymerase chain reaction mix containing the nucleic acid to an analysis unit in the channel for analysis.

In one embodiment the present invention provides polymerase chain reaction system for analyzing a sample that includes nucleic acid. The system includes a flow channel, magnetic beads, ethanol, a polymerase chain reaction master mix, a polymerase chain reaction chamber in the flow channel, a first magnet positioned at a pre polymerase chain reaction magnet position adjacent the polymerase chain reaction chamber in the flow channel, a second magnet positioned at a post polymerase chain reaction magnet position adjacent the polymerase chain reaction chamber in the flow channel, a waste stream for the magnetic beads, a post polymerase chain reaction reaction mix, and an analysis unit connected to the flow channel; wherein the nucleic acid is bound to the magnetic beads, wherein the magnetic beads with the nucleic acid bound to the magnetic beads is washed at the pre polymerase chain reaction magnet position by flowing the ethanol in the flow channel so that it flows over the magnetic beads with the nucleic acid bound to the magnetic beads, wherein the nucleic acid bound to the magnetic beads in the flow channel is amplified in the polymerase chain reaction chamber, wherein the magnetic beads and the nucleic acid is sequestered at the post polymerase chain reaction magnet position thereby separating the magnetic beads and the nucleic acid into a analysis stream containing the magnetic beads and a post polymerase chain reaction mix containing the nucleic acid, wherein the magnetic beads flow to waste in the flow channel; and wherein the post polymerase chain reaction mix containing the nucleic acid is analyzed in the analysis unit.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
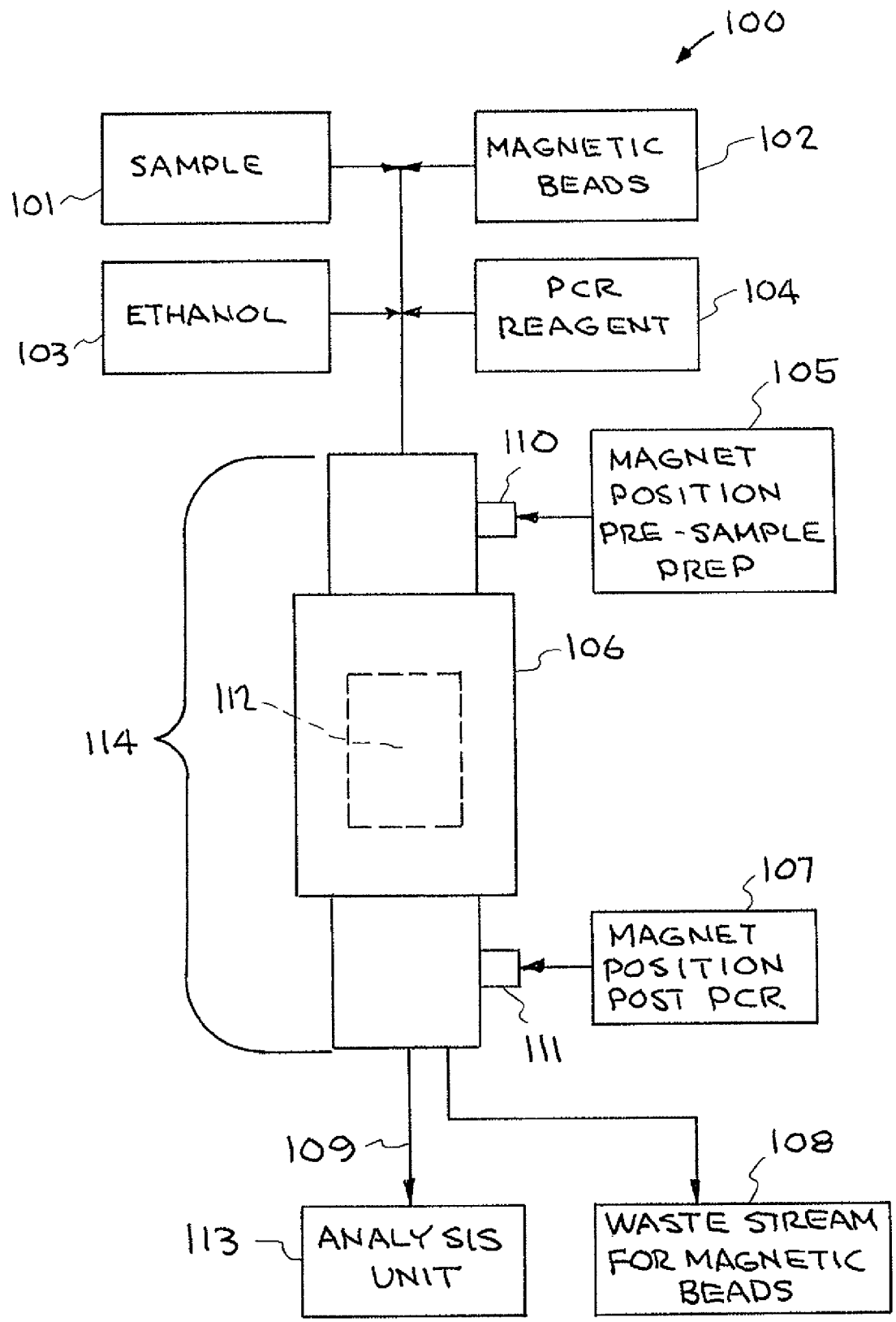
FIG. 1 illustrates one embodiment of a system constructed in accordance with the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1, an illustration of one embodiment of a polymerase chain reaction system for performing analysis of a sample is shown. The polymerase chain reaction system is designated generally by the reference numeral 100. The polymerase chain reaction system 100 is a system for analyzing a sample that includes nucleic acid. The system 100 includes the steps of providing magnetic beads; providing ethanol; providing a PCR master mix; providing a flow channel, the flow channel including a PCR chamber, a pre PCR magnet position adjacent the PCR chamber, and a post PCR magnet position adjacent the PCR chamber; mixing a chaotropic agent with the magnetic beads so that the nucleic acid is bound to the magnetic beads; flowing the magnetic beads with the nucleic acid bound to the magnetic beads to the pre PCR magnet position in the flow channel; washing the magnetic beads with the nucleic acid bound to the magnetic beads at the pre PCR magnet position by flowing the ethanol in the flow channel so that it flows over the magnetic beads with the nucleic acid bound to the magnetic beads; flowing the magnetic beads with the nucleic acid bound to the magnetic beads in the flow channel into the PCR chamber; amplifying the nucleic acid in the PCR chamber; flowing the magnetic beads with the nucleic acid bound to the magnetic beads to the post PCR magnet position in the flow channel; sequestering the magnetic beads at the post PCR magnet position separating the magnetic beads and the nucleic acid into a analysis stream containing the magnetic beads and a post PCR reaction mix containing the nucleic acid, flowing the magnetic beads to waste in the flow channel; and flowing the post PCR reaction mix containing the nucleic acid to an analysis unit in the channel for analysis.

The polymerase chain reaction system 100 includes the following structural components: sample 101, magnetic beads 102, ethanol 103, PCR master mix 104, pre PCR magnet position 105, PCR chamber 106, post PCR magnet position 107, waste stream for magnetic beads 108, post PCR reaction mix sent to analysis 109, magnet 110, magnet 111, PCR master mix plug 112, an analysis unit 113, and a channel 114.

The structural components of the polymerase chain reaction system for performing analysis of a sample having been described, the operation of the system 100 will now be considered. Equal volumes of sample 101 and a chaotropic agent such as Guanidine isothiocyanate are mixed with the magnetic beads 102. The nucleic acid from the sample 101 is bound to the magnetic beads 102 enroute to the PCR reaction chamber 106 through channel 114. The magnet 110 is moved into the "on" position at pre PCR magnet position 105 and the sample 101 is flowed over the magnet 110 at a rate of 1 µl/sec. The magnetic beads 102 containing the bound nucleic acid are captured over the magnet 110 at magnet position 105 as the sample 110 flows over it. The beads 102 are washed with 70% solution of ethanol 103 flowed over them.

The PCR master mix plug 112 is positioned next over the magnetic beads 102 at magnet position 105. The magnet 110 is then disengaged and the PCR master mix plug 112 containing the magnetic beads 102 is moved into the PCR reaction chamber 106. Amplifying the nucleic acid in the PCR reaction chamber by PCR.

After amplification of the nucleic acid, the PCR plug 112 containing the amplified product along with the magnetic beads 102 is moved downstream at a rate of 1 µl/sec. The downstream magnet 111 is moved into the "on" position and the beads 102 are sequestered out of solution. The post-PCR reaction 109 is sent to the analysis unit 113 for analysis and the magnetic beads 102 are sent to the waste stream 108 along with carrier fluid.

Figure 2:
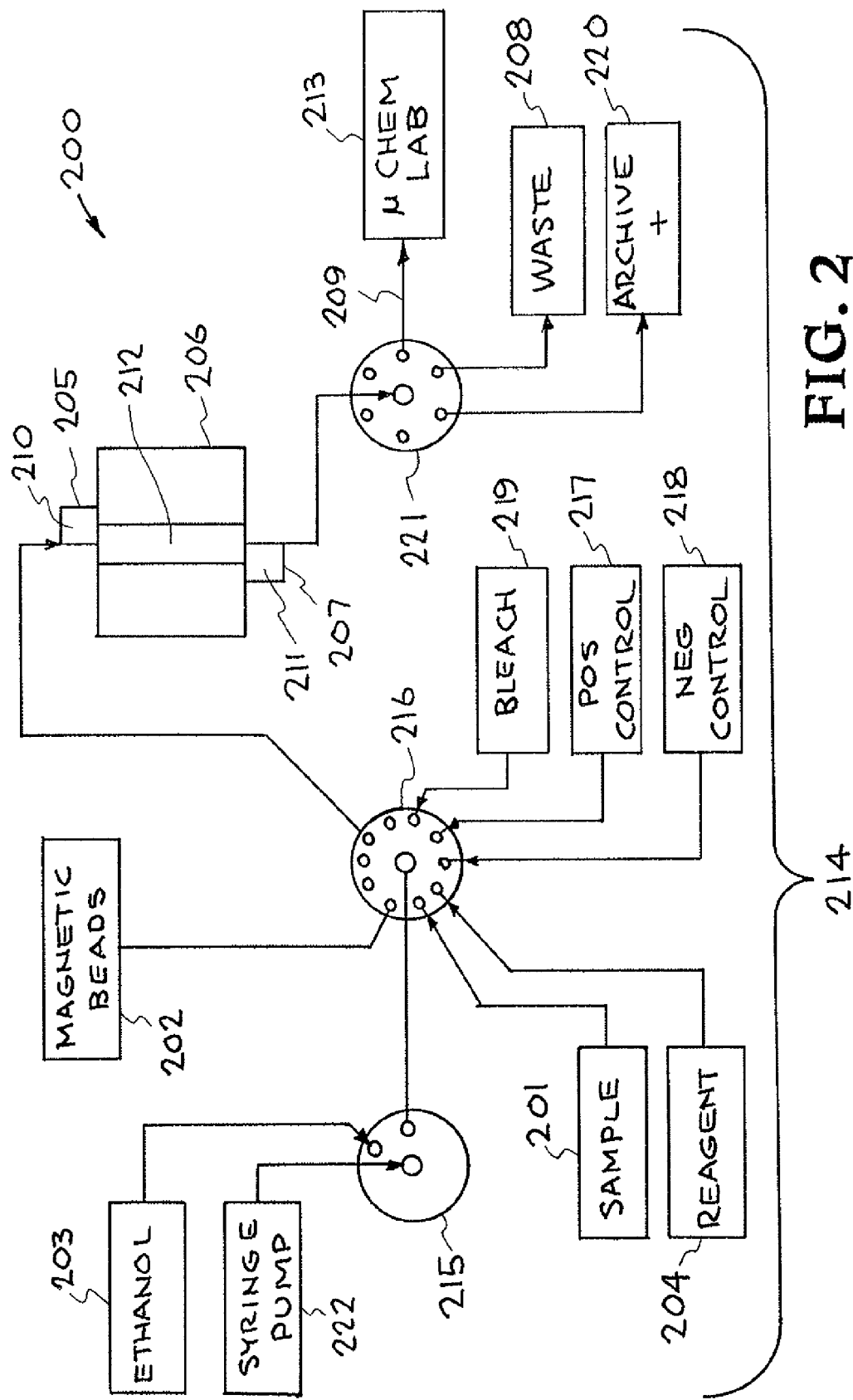
FIG. 2 illustrates another embodiment of a system constructed in accordance with the present invention.

Referring now to FIG. 2, an illustration of another embodiment of a polymerase chain reaction system for performing analysis of a sample is shown. The polymerase chain reaction system is designated generally by the reference numeral 200.

The polymerase chain reaction system 200 includes the following structural components: sample 201, magnetic beads 202, ethanol 203, PCR master mix 204, pre PCR magnet position 205, PCR chamber 206, post PCR magnet position 207, waste stream for magnetic beads 208, post PCR reaction mix sent to analysis 209, magnet 210, magnet 211, PCR master mix plug 212, an analysis unit 213, a channel 214, a 2 port valve 215, a 10 port valve 216, a positive control 217, a negative control 218, bleach 219, archive 220, a 6 port valve 221, and a syringe pump 222.

The structural components of the polymerase chain reaction system for performing analysis of a sample having been described, the operation of the system 200 will now be considered. The nucleic acid from the sample 201 is bound to the magnetic beads 202 enroute to the PCR reaction chamber 206 through channel 214. The magnetic beads 202 are mixed in line along with the chaotropic agent such as 3M Guanidine Isothiocyanate containing 10% Ethanol. The flow rate of mixing is set to 10µl/sec with 5 µl liquid volume of each of the reagents i.e the guanidine solution, magnetic beads 202 and sample 201 using the 10 port valve 216. This flow rate and volume was determined to be required in order to get efficient mixing of the sample with the magnetic beads 202 and lysing agent 219.

The magnet 210 is moved into the "on" position at pre PCR magnet position 205 and the sample 201 is flowed over the magnet 210. The magnetic beads 202 containing the bound nucleic acid are captured over the magnet 210 at magnet position 205 as the sample 210 flows over it.

The mix is then sent through the flow channel 214 at a speed of 1 µl/sec. This flow rate has been found to be important for binding of the magnetic beads 202 to the magnet 210.

The magnet 210 is positioned right above the reaction chamber 206. Once the magnetic beads 202 are collected on the magnet 210, the beads 202 are washed once with 70% Ethanol 203 followed by water. The PCR reagent 204 is then metered to position on the magnetic beads 202. For applicant's purposes 10 μl of amplification reagents either, PCR or Reverse transcriptase PCR (RT-PCR) reagent was used for the amplification.

Once the amplification mix is positioned on the magnetic beads 202 the top magnet 210 is released and the reaction along with the beads 202 is moved into the reaction chamber 206. Amplification is carried out on the magnetic beads 202 in the reaction chamber 206. Applicant has accomplished both Reverse Transcriptase-PCR, and PCR for spores, bacterial cells and RNA viruses in this manner. The amplification reagent in applicants' assay contained electrophoretic tags (eTag) attached to the probe, forward and reverse primers, reverse transcriptase enzyme and DNA polymerase. Since the polymerase enzyme has a 5'-3' exonuclease activity, on encountering the probe the eTag is released. This amplification process is commonly known as the Taqman reaction.

The released tag is then detected by capillary electrophoresis. On completion of amplification, the amplified reaction along with the magnetic beads 202 is moved through the tubing 209 toward the capillary electrophoresis system know as the μChem lab 213 where it is mixed with a separation reagent and electrophoretic markers. En route to the μChem Lab 213, the magnetic beads 202 are removed by another magnet 211 that is placed below the reaction chamber 206.

After amplification of the nucleic acid, the PCR plug 212 containing the amplified product along with the magnetic beads 202 is moved downstream at a rate of 1 μl/sec. The downstream magnet 211 is moved into the "on" position and the beads 202 are sequestered out of solution. The post-PCR reaction 209 is sent to the analysis unit 213 for analysis and the magnetic beads 202 are sent to the waste stream 208 along with carrier fluid.

Once the amplified reaction is free of the magnetic beads 202 the magnet 211 is released so that the magnetic beads 202 can flow out into the waste 208 and the flow line is decontaminated using 10% Bleach followed by water rinse. The instrument 200 is ready for the next sample introduction.

The polymerase chain reaction system 200 is a system for analyzing a sample that includes nucleic acid. The system 200 includes the steps of providing magnetic beads; providing ethanol; providing a PCR master mix; providing a flow channel, the flow channel including a PCR chamber, a pre PCR magnet position adjacent the PCR chamber, and a post PCR magnet position adjacent the PCR chamber; mixing a chaotropic agent with the magnetic beads so that the nucleic acid is bound to the magnetic beads; flowing the magnetic beads with the nucleic acid bound to the magnetic beads to the pre PCR magnet position in the flow channel; washing the magnetic beads with the nucleic acid bound to the magnetic beads at the pre PCR magnet position by flowing the ethanol in the flow channel so that it flows over the magnetic beads with the nucleic acid bound to the magnetic beads; flowing the magnetic beads with the nucleic acid bound to the magnetic beads in the flow channel into the PCR chamber; amplifying the nucleic acid in the PCR chamber; flowing the magnetic beads with the nucleic acid bound to the magnetic beads to the post PCR magnet position in the flow channel; sequestering the magnetic beads at the post PCR magnet position separating the magnetic beads and the nucleic acid into a waste stream containing the magnetic beads and a post PCR reaction mix containing the nucleic acid, flowing the magnetic beads to waste in the flow channel; and flowing the post PCR reaction mix containing the nucleic acid to an analysis unit in the channel for analysis.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A polymerase chain reaction method of analyzing a sample that includes nucleic acid, comprising the steps of:
providing the sample that includes nucleic acid;
providing magnetic beads;
providing ethanol;
providing a polymerase chain reaction master mix;
providing a flow channel, said flow channel including a polymerase chain reaction chamber, a pre polymerase chain reaction magnet position adjacent said polymerase chain reaction chamber, and a post polymerase chain reaction magnet position adjacent said polymerase chain reaction chamber;
mixing a chaotropic agent with the sample that includes nucleic acid and with said magnetic beads to enable the nucleic acid to be bound to said magnetic beads;
flowing said magnetic beads with the nucleic acid bound to said magnetic beads to said pre polymerase chain reaction magnet position in said flow channel;
washing said magnetic beads with the nucleic acid bound to said magnetic beads at said pre polymerase chain reaction magnet position by flowing said ethanol in said flow channel so that it flows over said magnetic beads with the nucleic acid bound to said magnetic beads;
flowing said magnetic beads with the nucleic acid bound to said magnetic beads in said flow channel into said polymerase chain reaction chamber;
amplifying the nucleic acid in said polymerase chain reaction chamber providing amplified nucleic acid;
flowing said magnetic beads and said amplified nucleic acid to said post polymerase chain reaction magnet position in said flow channel;
sequestering said magnetic beads at said post polymerase chain reaction magnet position separating said magnetic beads and said amplified nucleic acid into a waste stream containing said magnetic beads and a post polymerase chain reaction mix containing said amplified nucleic acid,
flowing said magnetic beads to waste in said flow channel; and
flowing said post polymerase chain reaction mix containing said amplified nucleic acid to an analysis unit in said channel for analysis.

2. The polymerase chain reaction method of analyzing a sample of claim 1 wherein said steps of providing ethanol and washing said magnetic beads with the nucleic acid bound to said magnetic beads at said pre polymerase chain reaction magnet position by flowing said ethanol in said flow channel so that it flows over said magnetic beads with the nucleic acid bound to said magnetic beads comprises providing a seventy percent solution of ethanol and washing said magnetic beads with the nucleic acid bound to said magnetic beads at said pre polymerase chain reaction magnet position by flowing said seventy percent solution of ethanol in said flow channel so that said seventy percent solution of ethanol flows over said magnetic beads with the nucleic acid bound to said magnetic beads.

3. The polymerase chain reaction method of analyzing a sample of claim 1 wherein said steps of mixing a chaotropic agent with the sample that includes nucleic acid and with said magnetic beads to enable the nucleic acid to be bound to said magnetic beads comprises mixing 3M Guanidine Isothiocyanate containing ten percent ethanol with the sample that includes nucleic acid and with said magnetic beads to enable the nucleic acid to be bound to said magnetic beads.

4. The polymerase chain reaction method of analyzing a sample of claim 1 wherein said step of flowing said magnetic beads with the nucleic acid bound to said magnetic beads to said pre polymerase chain reaction magnet position in said flow channel comprises flowing said magnetic beads at a speed of 1 µ/sec.

5. A polymerase chain reaction system for analyzing a sample that includes nucleic acid, comprising:
   a sample that includes nucleic acid,
   a chaotropic agent,
   a flow channel,
   magnetic beads,
   ethanol,
   a polymerase chain reaction master mix,
   a polymerase chain reaction chamber in said flow channel,
   a first magnet positioned at a pre polymerase chain reaction magnet position adjacent said polymerase chain reaction chamber in said flow channel,
   a second magnet positioned at a post polymerase chain reaction magnet position adjacent said polymerase chain reaction chamber in said flow channel,
   a waste stream for said magnetic beads,
   a post polymerase chain reaction reaction mix, and
   an analysis unit connected to said flow channel,
   wherein the nucleic acid is bound to said magnetic beads,
   wherein said magnetic beads are mixed with said chotropic agent enabling the nucleic acid to be bound to said magnetic beads,
   wherein said magnetic beads with the nucleic acid bound to said magnetic beads are washed at said pre polymerase chain reaction magnet position by flowing said ethanol in said flow channel so that it flows over said magnetic beads with the nucleic acid bound to said magnetic beads,
   wherein the nucleic acid bound to said magnetic beads in said flow channel is amplified in said polymerase chain reaction chamber providing amplified nucleic acid,
   wherein said magnetic beads and said amplified nucleic acid are sequestered at said post polymerase chain reaction magnet position thereby separating said magnetic beads and said amplified nucleic acid into a waste stream containing said magnetic beads and a post polymerase chain reaction mix containing said amplified nucleic acid,
   wherein said magnetic beads flow to waste in said flow channel; and
   wherein said post polymerase chain reaction mix containing said amplified nucleic acid is analyzed in said analysis unit.

6. The polymerase chain reaction system for analyzing a sample of claim 5 wherein said ethanol is a seventy percent solution of ethanol.

7. A polymerase chain reaction apparatus for analyzing a sample that includes nucleic acid, comprising:
   a sample that includes nucleic acid,
   a chaotropic agent,
   a flow channel;
   a pump connected to said flow channel,
   ethanol;
   a pump and ethanol multi-position valve connected to said flow channel;
   magnetic beads;
   a polymerase chain reaction master mix;
   a sample multi-position valve connected to the sample, connected to said pump and ethanol multi-position valve, connected to said magnetic beads, and connected to said polymerase chain reaction master mix;
   a polymerase chain reaction chamber in said flow channel, said polymerase chain reaction chamber connected to said sample multi-position valve;
   a first magnet positioned at a pre polymerase chain reaction magnet position adjacent said polymerase chain reaction chamber in said flow channel;
   a second magnet positioned at a post polymerase chain reaction magnet position adjacent said polymerase chain reaction chamber in said flow channel;
   a waste stream for said magnetic beads;
   a post polymerase chain reaction mix;
   an analysis unit connected to said flow channel; and
   a waste multi-position valve connected to said polymerase chain reaction chamber;
   wherein said magnetic beads are mixed with said chotropic agent enabling the nucleic acid to be bound to said magnetic beads,
   wherein said magnetic beads with the nucleic acid bound to said magnetic beads are washed at said pre polymerase chain reaction magnet position by flowing said ethanol in said flow channel so that it flows over said magnetic beads with the nucleic acid bound to said magnetic beads,
   wherein the nucleic acid bound to said magnetic beads in said flow channel is amplified in said polymerase chain reaction chamber providing amplified nucleic acid,
   wherein said magnetic beads and said amplified nucleic acid are sequestered at said post polymerase chain reaction magnet position thereby separating said magnetic beads and said amplified nucleic acid into a waste stream containing said magnetic beads and a post polymerase chain reaction mix containing said amplified nucleic acid,
   wherein said magnetic beads flow to waste in said flow channel; and
   wherein said post polymerase chain reaction mix containing said amplified nucleic acid is analyzed in said analysis unit.

8. The polymerase chain reaction apparatus for analyzing a sample of claim 7 wherein said pump and ethanol multi-position valve is a two port rotational multi-position valve.

9. The polymerase chain reaction apparatus for analyzing a sample of claim 7 wherein said sample multi-position valve is a ten port rotational multi-position valve.

10. The polymerase chain reaction apparatus for analyzing a sample of claim 7 wherein said sample multi-position valve is a six port rotational multi-position valve.

11. The polymerase chain reaction apparatus for analyzing a sample of claim 7 wherein said ethanol is a seventy percent solution of ethanol.

* * * * *